(12) United States Patent
Schwingendorf et al.

(10) Patent No.: US 8,141,187 B2
(45) Date of Patent: Mar. 27, 2012

(54) SLEEPY HEAD'S/NECK PILLOW INVENTION

(76) Inventors: Alice Jean Schwingendorf, Tokyo (JP); Gabriel Olivier Durand, Tokyo (JP)

( * ) Notice: Subject to any disclaimer, the term of this patent is extended or adjusted under 35 U.S.C. 154(b) by 0 days.

(21) Appl. No.: 12/659,814

(22) Filed: Mar. 22, 2010

(65) Prior Publication Data

US 2011/0225736 A1    Sep. 22, 2011

(51) Int. Cl.
A47G 9/10 (2006.01)
(52) U.S. Cl. .................. 5/636; 5/640; 297/393
(58) Field of Classification Search .............. 5/636, 637, 5/640, 643; 297/393, 397
See application file for complete search history.

(56) References Cited

U.S. PATENT DOCUMENTS

| | | | | |
|---|---|---|---|---|
| 1,510,187 A * | 9/1924 | Martin | | 297/393 |
| 1,579,585 A * | 4/1926 | Wieder et al. | | 297/394 |
| 3,285,658 A * | 11/1966 | Cleveland | | 297/395 |
| 4,285,081 A * | 8/1981 | Price | | 5/637 |
| 4,345,347 A * | 8/1982 | Kantor | | 5/644 |
| 4,562,833 A * | 1/1986 | Pujals, Jr. | | 602/18 |
| 4,617,691 A * | 10/1986 | Monti et al. | | 5/640 |
| 4,708,129 A * | 11/1987 | Pujals, Jr. | | 602/18 |
| 4,738,488 A * | 4/1988 | Camelio | | 297/383 |
| 5,505,523 A * | 4/1996 | Wang | | 297/393 |
| 5,778,469 A * | 7/1998 | Festa | | 5/640 |
| 5,974,607 A * | 11/1999 | Smith | | 5/636 |
| 6,123,389 A | 9/2000 | O'Connor et al. | | |
| 6,305,749 B1 | 10/2001 | O'Connor et al. | | |
| 6,786,554 B1 * | 9/2004 | Zahiri | | 297/393 |
| 6,893,094 B2 | 5/2005 | O'Connor et al. | | |
| 7,197,781 B2 * | 4/2007 | Ramsbottom et al. | | 5/636 |
| 7,644,990 B2 * | 1/2010 | Pearson | | 297/393 |
| 7,908,692 B2 * | 3/2011 | Lange | | 5/636 |
| 2001/0054837 A1 | 12/2001 | O'Connor | | |
| 2005/0102758 A1 * | 5/2005 | Ramsbottom et al. | | 5/636 |
| 2005/0179300 A1 | 8/2005 | O'Connor et al. | | |
| 2006/0244300 A1 | 11/2006 | Watson Savage | | |
| 2011/0094035 A1 * | 4/2011 | Tansingco | | 5/644 |

FOREIGN PATENT DOCUMENTS

| | | |
|---|---|---|
| AU | 8872501 A | 4/2002 |
| DE | 10196653 B | 12/2005 |
| GB | 2382985 A | 6/2003 |
| GB | 2382985 B | 4/2005 |
| JP | 3015207 U | 8/1995 |
| WO | 02/24031 A1 | 3/2002 |

OTHER PUBLICATIONS

International Search Report mailed Apr. 26, 2011 in corresponding PCT application No. PCT/JP2011/000779.

* cited by examiner

*Primary Examiner* — Robert G Santos
(74) *Attorney, Agent, or Firm* — Nields, Lemack & Frame, LLC

(57) ABSTRACT

The present invention is related to a supportive head and neck pillow with a supportive bone structure inside the pillow. The invention is used for head and neck support, and comfort while sleeping sitting up during transportation. It can also be used for head and neck support for people who have neck injuries, or to prevent neck injuries during transportation. The main components are made up of two things; a pillow with a bone structure support inside the pillow and a clip/strap system.

7 Claims, 14 Drawing Sheets

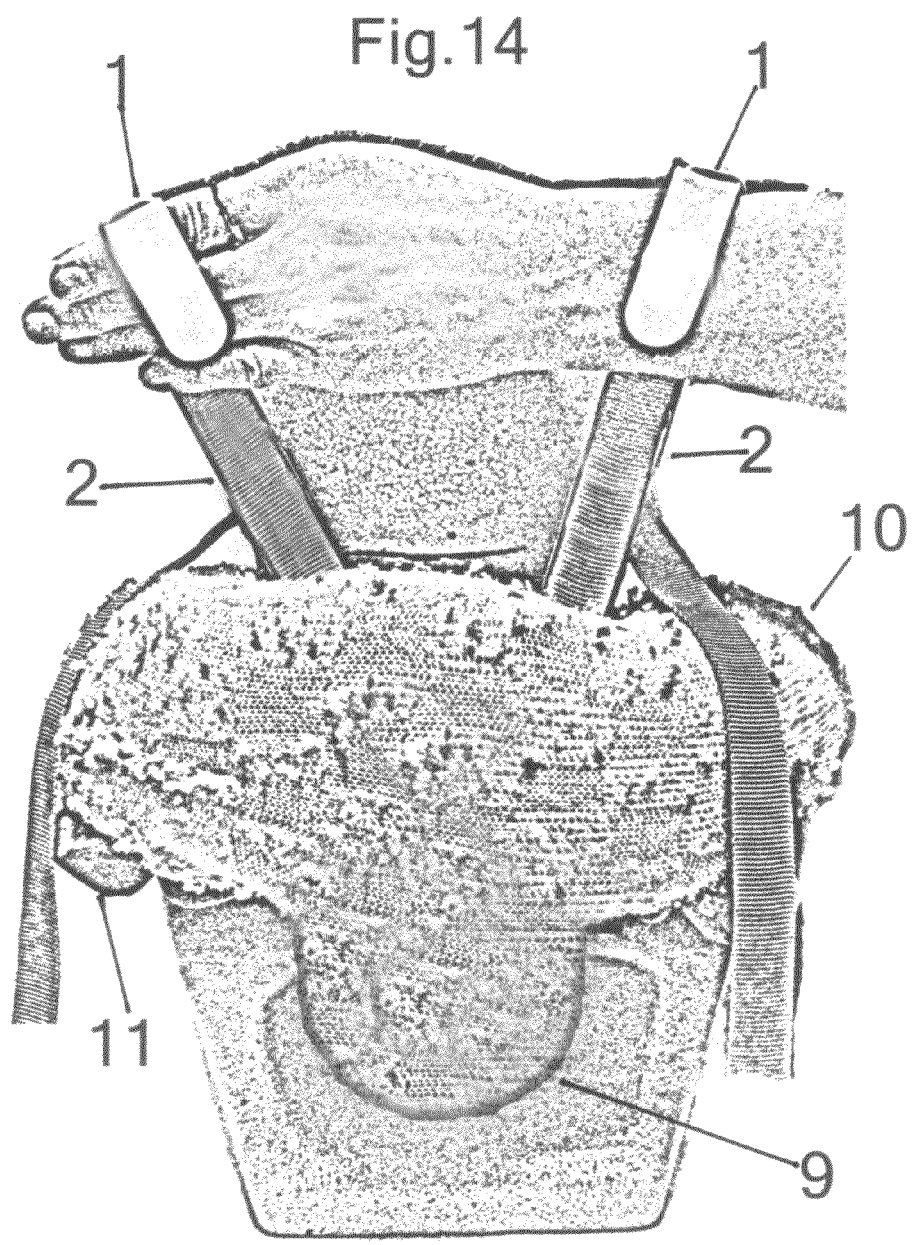

SLEEPY HEAD'S/NECK PILLOW INVENTION

FIELD OF THE INVENTION

The invention is a supportive heads neck pillow with a supportive bone structure inside the pillow. The invention is used for head and neck support, and comfort while sleeping sitting up during transportation.

BACKGROUND

The reason we thought about this invention, it is because like us, and millions of other people can't sleep comfortably when sitting up during traveling (airplane, train, bus trip, and passenger in cars, etc. . . . ). Another reason we thought about this invention is because it is suitable for people who have neck injuries, it will help keep their head, and neck secure during traveling (airplane, train, bus trip, and passenger in cars, etc. . . . ). It will also procure a great feeling of comfort. After research, and testing many different head/neck pillows on the market, not one was satisfactory to give the support, and comfort while sitting up sleeping. We decided to invent a head/neck pillow that would have a great comfort, and with inside the pillow have a supportive bone structure that will conform, fit the shape of the neck with great support.

SUMMARY

The Sleepy Head's/Neck Pillow is a new style supportive pillow that will give your neck, head, and upper back support. It will give great comfort while sleeping while sitting up during transportation.

The invention is related to a supportive heads neck pillow with a supportive bone structure inside the pillow. The invention is used for head and neck support, and comfort while sleeping sitting up during transportation. It can also be used for head and neck support for people who have neck injuries, or to prevent neck injuries during transportation. The main components are made up of two things. That is, the pillow with the supportive bone structure inside it, which gives support and comfort to the head, neck, and upper back, and the supportive, adjustable straps which are connected to the adjustable clips which give the extra support to the pillow when connected to a seat.

That is, the invention has the following constitutions:
(1) A sleepy heads neck pillow comprising a pillow with a bone structure support inside the pillow and a clip/strap system that is fixed to the bone structure, wherein the bone structure support is fully incased in the pillow, and the bone structure support consists of three parts; a neck bone support, an arm bone, and an upper back bone.
(2) The sleepy heads neck pillow according to (1), wherein the adjustable clip/strap system comprises a supportive adjustable strap which is connected to the clip system which is fixed to the bone structure.
(3) The sleepy heads neck pillow according to (1) or (2), wherein the bone structure support is made of one piece.
(4) A sleepy heads neck pillow consisting of a pillow, a bone structure support inside the pillow, an adjustable clip/strap system, shoulder support padding, a pillow cover, and a clip system cover.
(5) A clip system for a sleepy heads neck pillow, which closes automatically by the weight of the pillow when it is fixed on a seat.

BRIEF DESCRIPTION OF THE DRAWINGS

FIG. 14 illustrates a complete pillow and straps (back view without cover).

DETAILED DESCRIPTION

The sleepy heads neck pillow of the invention will help people sleep while sitting up. The reason that the sleepy heads neck pillow of the invention is unique is because there is a bone structure support inside the pillow that is connected to the clip/strap system.

The pillow ("Sleepy Heads Neck Pillow") shape is unique because of the shape of the bone structure that is fully incased in the pillow.

The bone structure support that consists of three parts; a neck bone support, an arm bone, and an upper back bone support, which is made to give maximum support and great comfort to the head, neck and upper back.

Since there is a clip/strap system that is secured to the seat it gives optimum support to the head, neck, and upper back.

Sleepy Heads Neck Pillow of the present invention is also unique because there is a shoulder padding support built into the pillow.

Sleepy Heads Neck Pillow of the present invention consists of five different main parts; a pillow, a bone structure, an adjustable clip/strap system, shoulder support padding, a pillow cover and a clip system cover.

Sleepy Heads Neck Pillow of the present invention is explained in more detail by referring to the attached figures.

Figure 1:
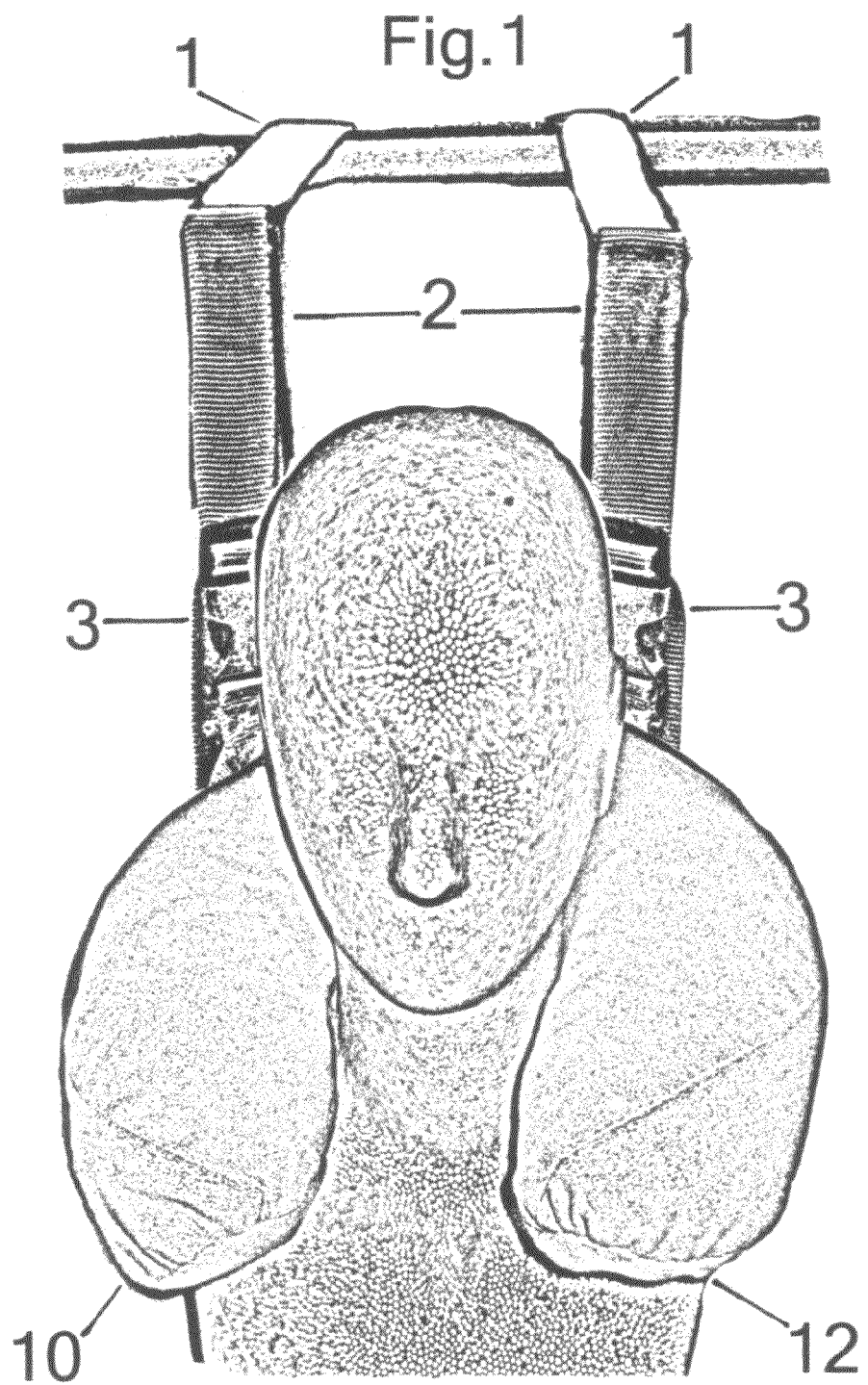
FIG. 1 illustrates a sleepy heads neck pillow with cover, strap system, and bone support belt.

FIG. 1 illustrates a sleepy heads neck pillow with cover, strap system, and bone support belt.

Figure 2:
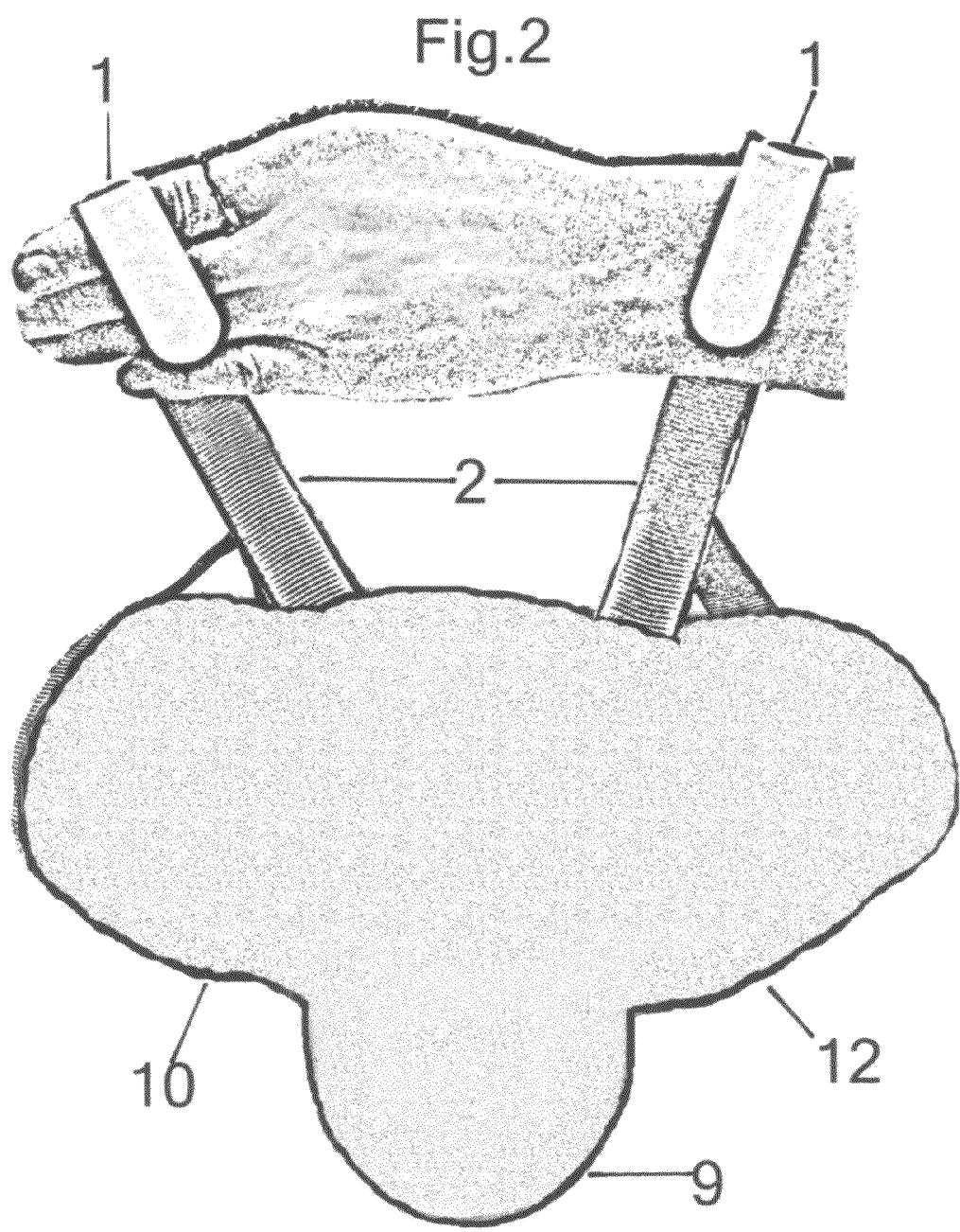
FIG. 2 illustrates a sleepy heads neck pillow with cover, back view with strap system, and bone.

FIG. 2 illustrates a sleepy heads neck pillow with cover, back view with strap system, and bone.

Figure 3:
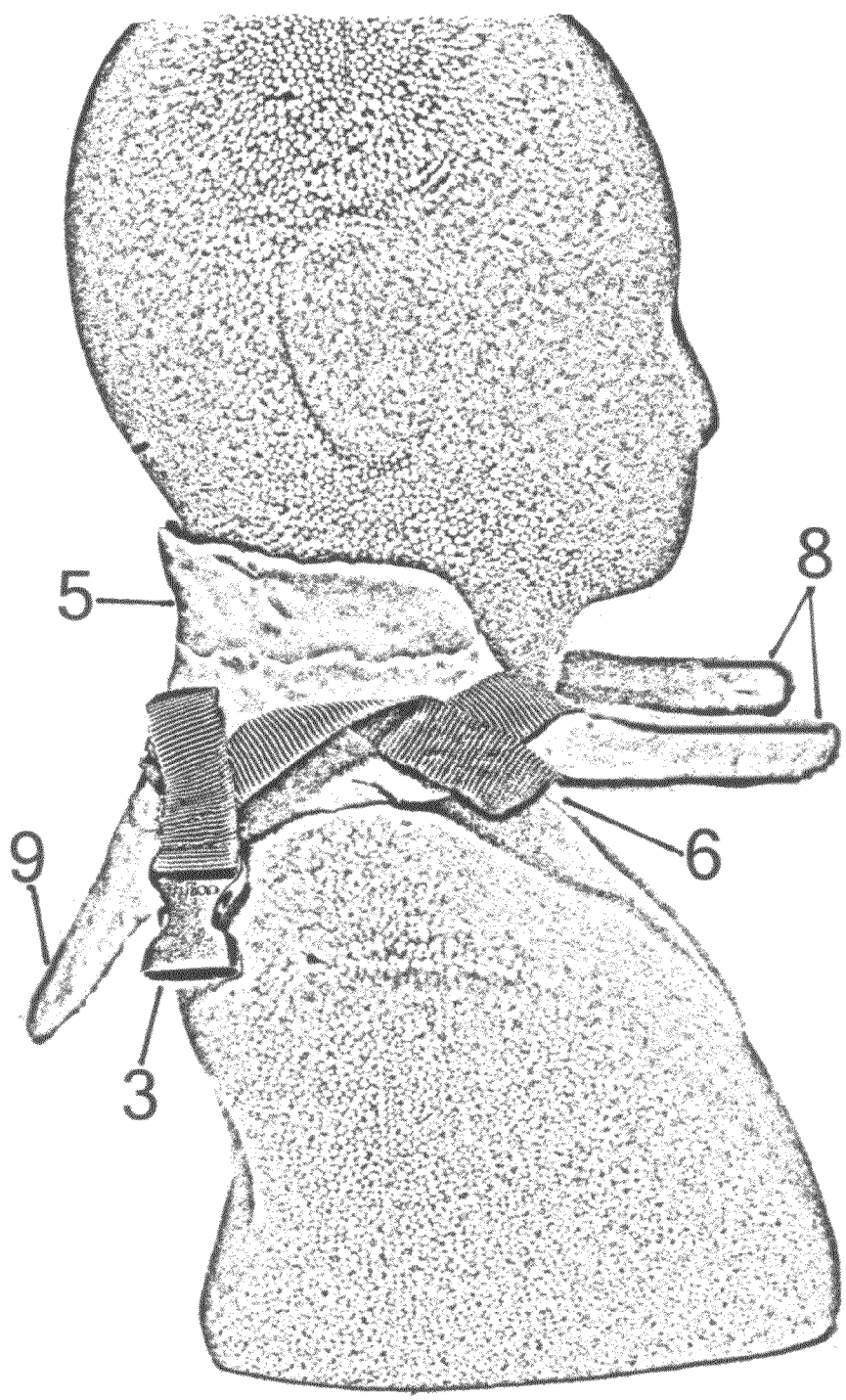
FIG. 3 shows a side view of bone structure.

FIG. 3 illustrates a side view of bone structure. The neck bone support part (5) will provide support and comfort to the neck. The arm bone (8) will support the weight of the head.

Figure 4:
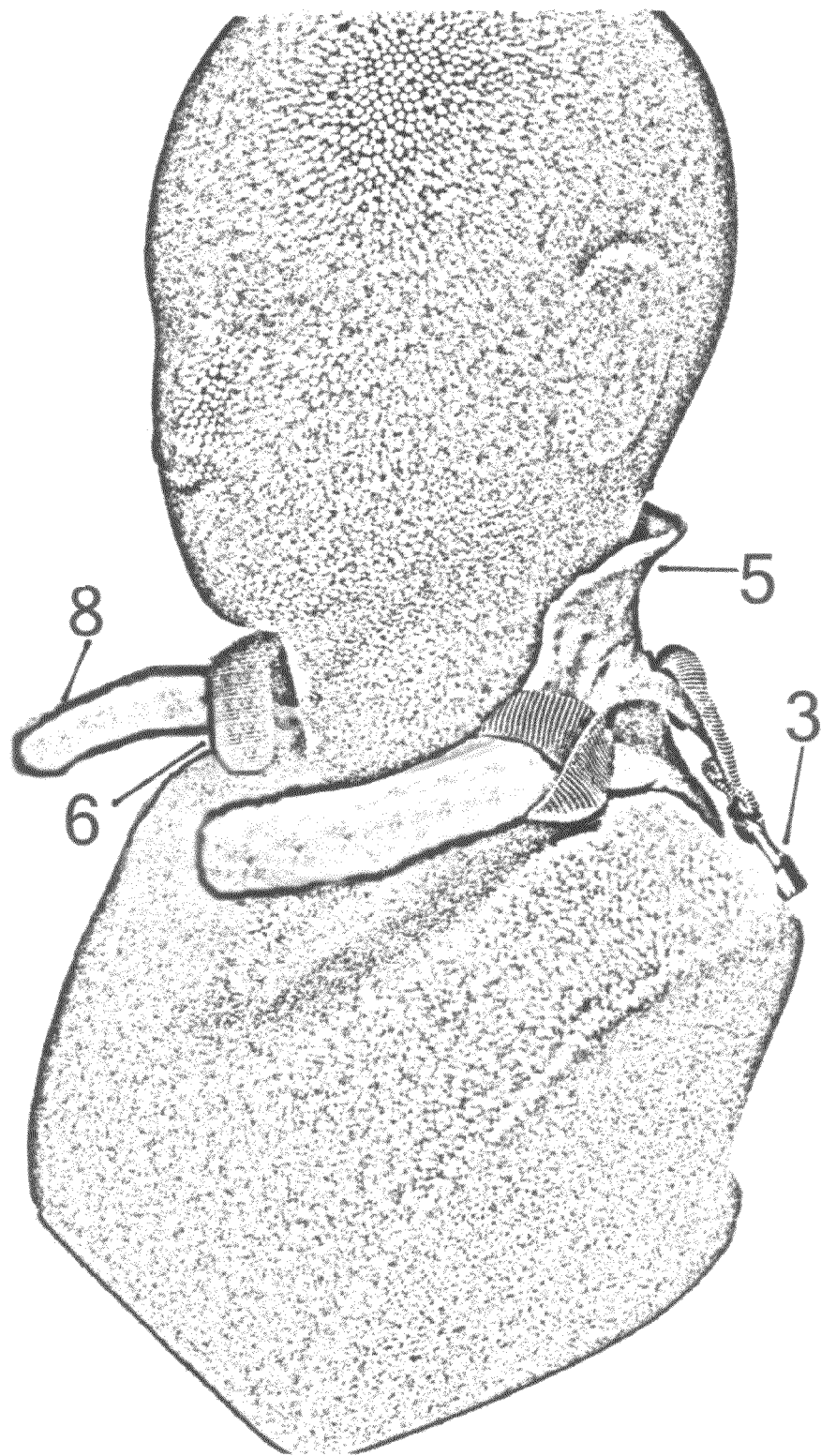
FIG. 4 shows ¾ side view of bone structure.

FIG. 4 illustrates ¾ side view of bone structure. Supportive arm strap (6) is on each side of the arm bone, which is connected to the bone structure.

Figure 5:
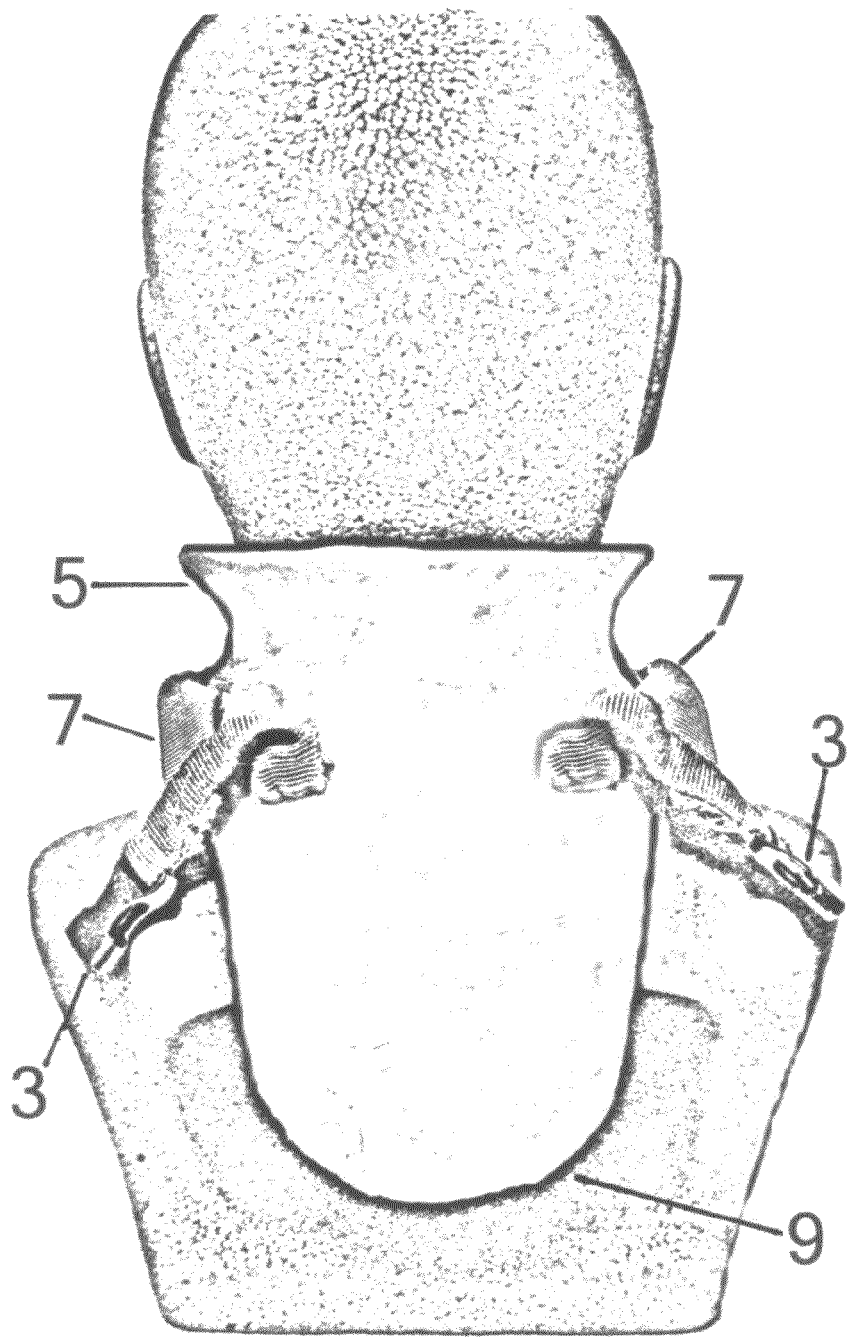
FIG. 5 shows a back face of bone structure.

FIG. 5 illustrates a back face of bone structure. The support belt (7) will be securely connected to the back of the bone structure. (9) indicates upper back bone support. The back bone part will support the upper back.

Figure 6:
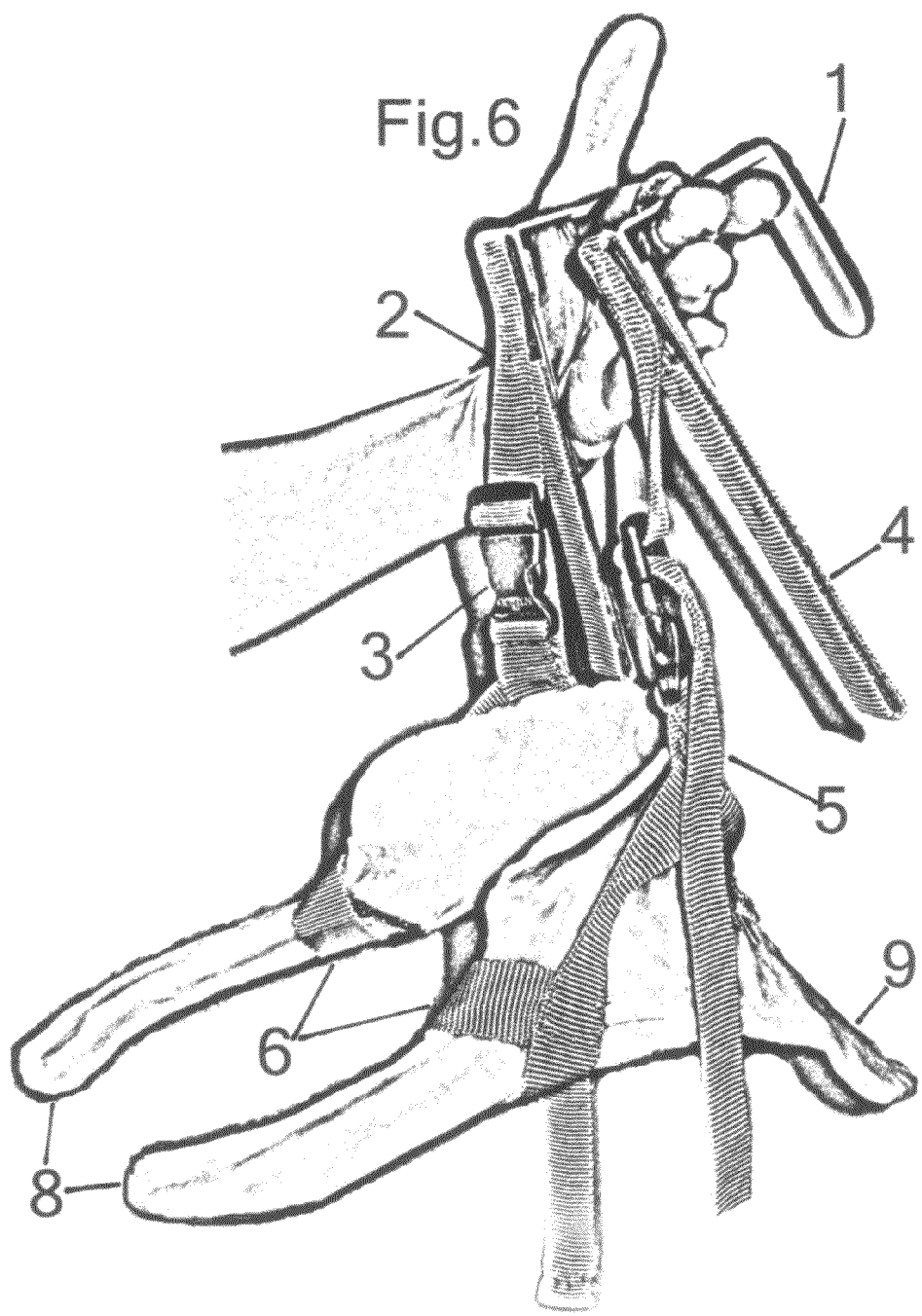
FIG. 6 illustrates a full strap system with bone structure outside pillow.

FIG. 6 illustrates a full strap system with bone structure outside pillow.

Figure 7:
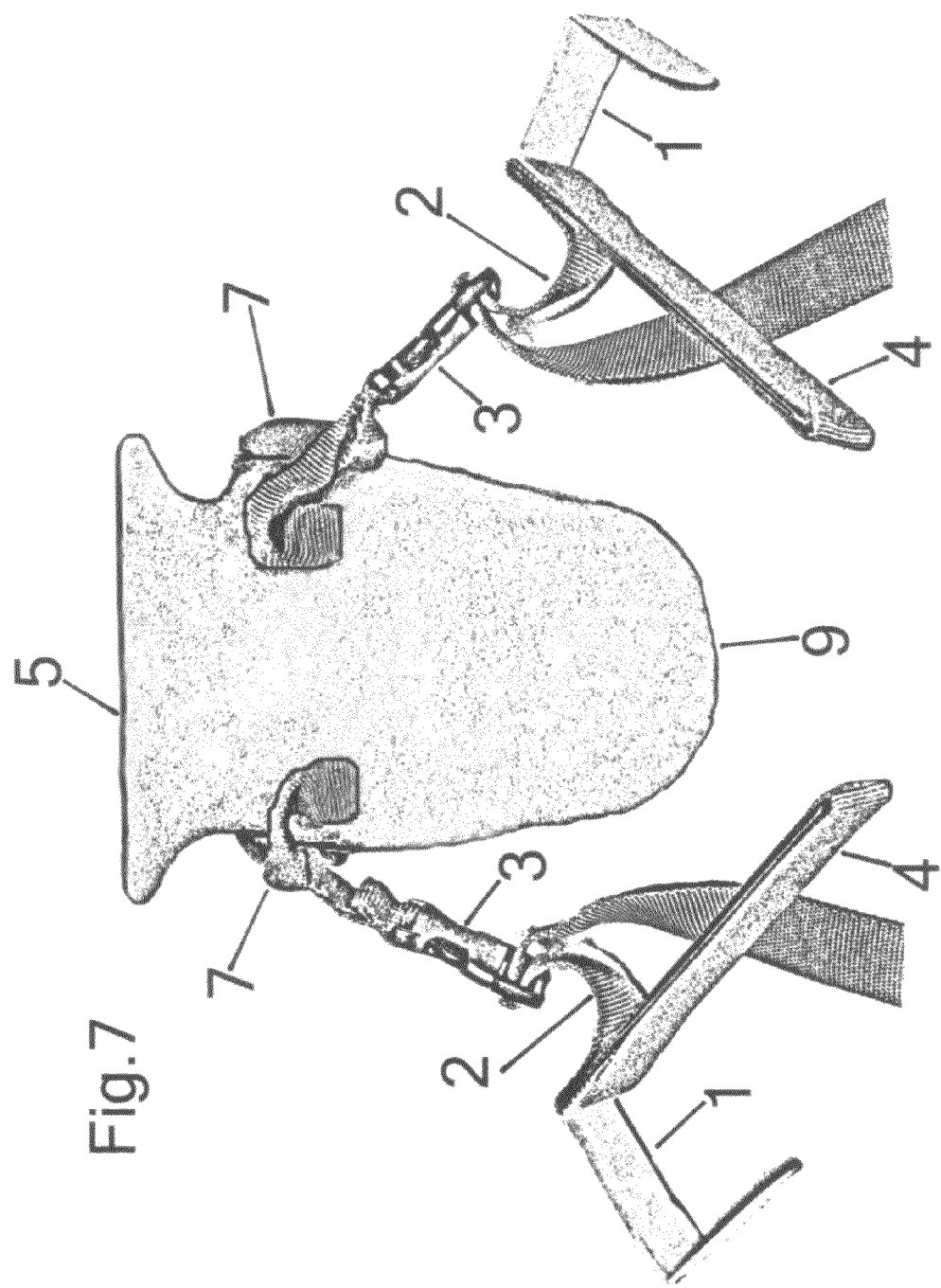
FIG. 7 illustrates a full strap system.

FIG. 7 illustrates a full strap system. The seat clips are adjustable for the thickness of the seats (car seats, airplane seats, etc.) Supportive seat brace also gives support on the seat. The seat strap length can be adjusted. The straps that are connected to the bone are detachable from the seat straps.

Figure 8:
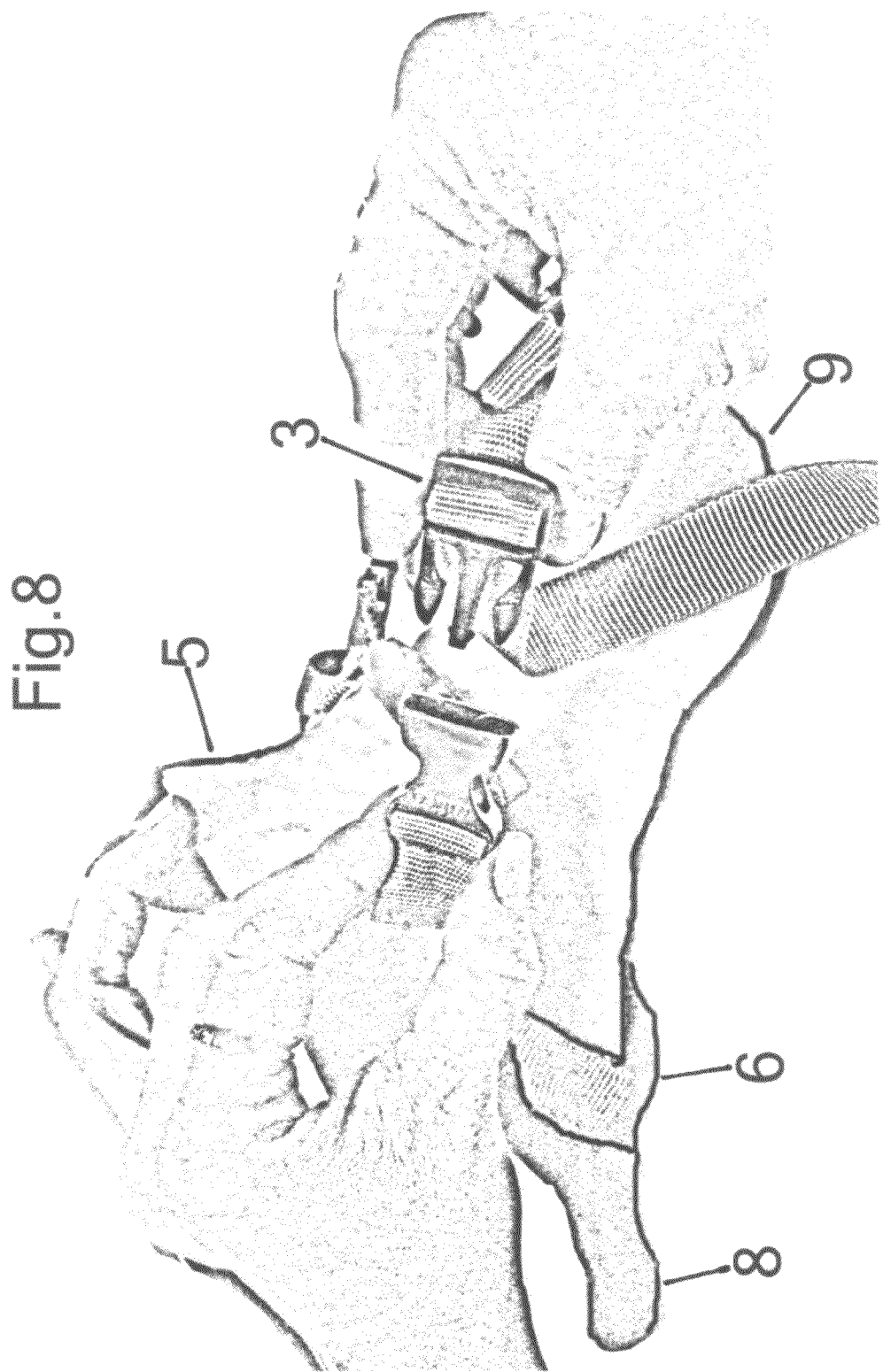
FIG. 8 illustrates a detachable clip system.

FIG. 8 illustrates a detachable clip system; clip on bone strap, clip on seat strap.

Figure 9:
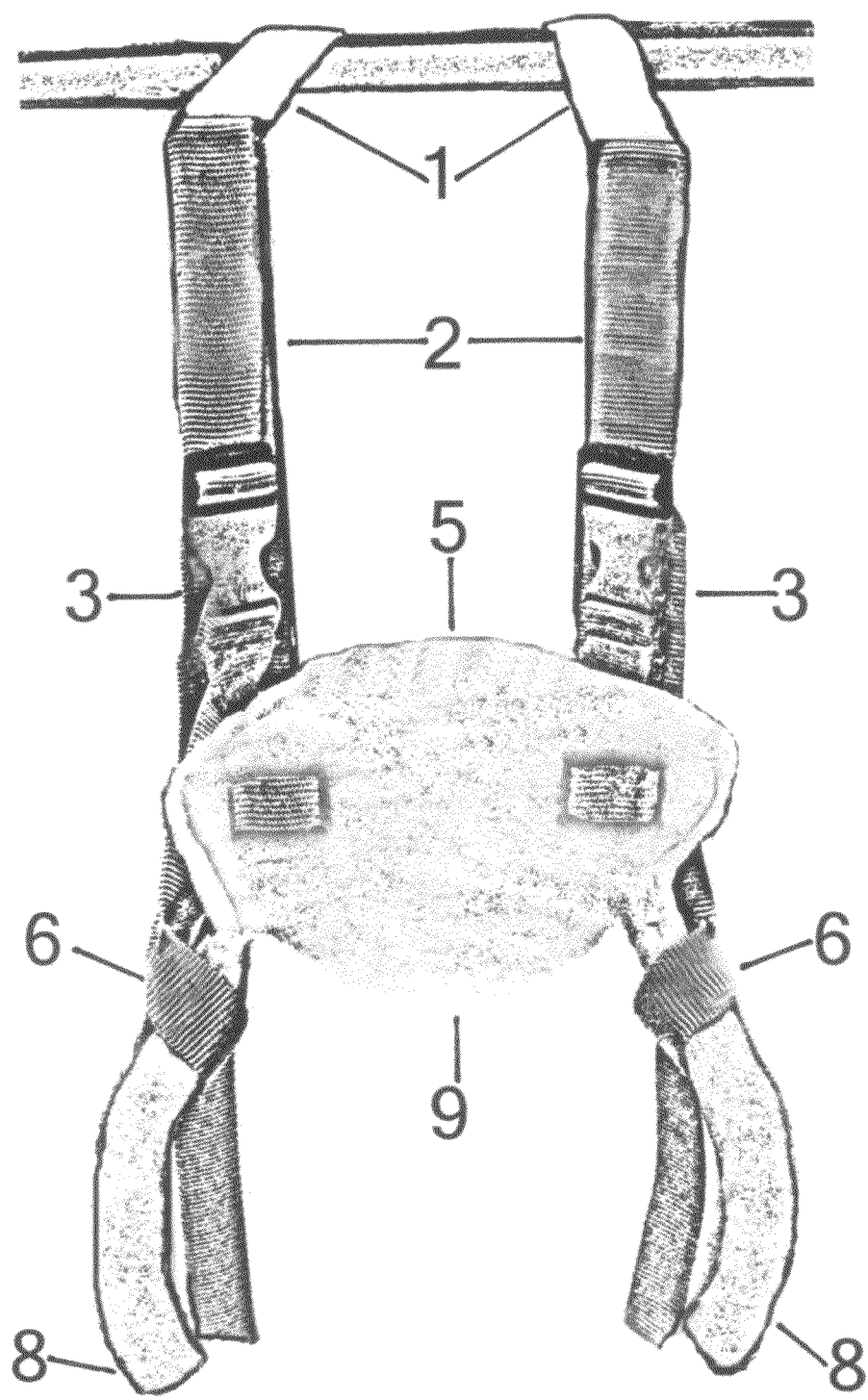
FIG. 9 shows a hanging strap view.

FIG. 9 shows a hanging strap view; indicating adjustable seat clips (1), adjustable seat straps (2), detachable clips (3), neck support bone (5), upper back bone support (9), supportive arm straps (6), and arm bone (8).

Figure 10:
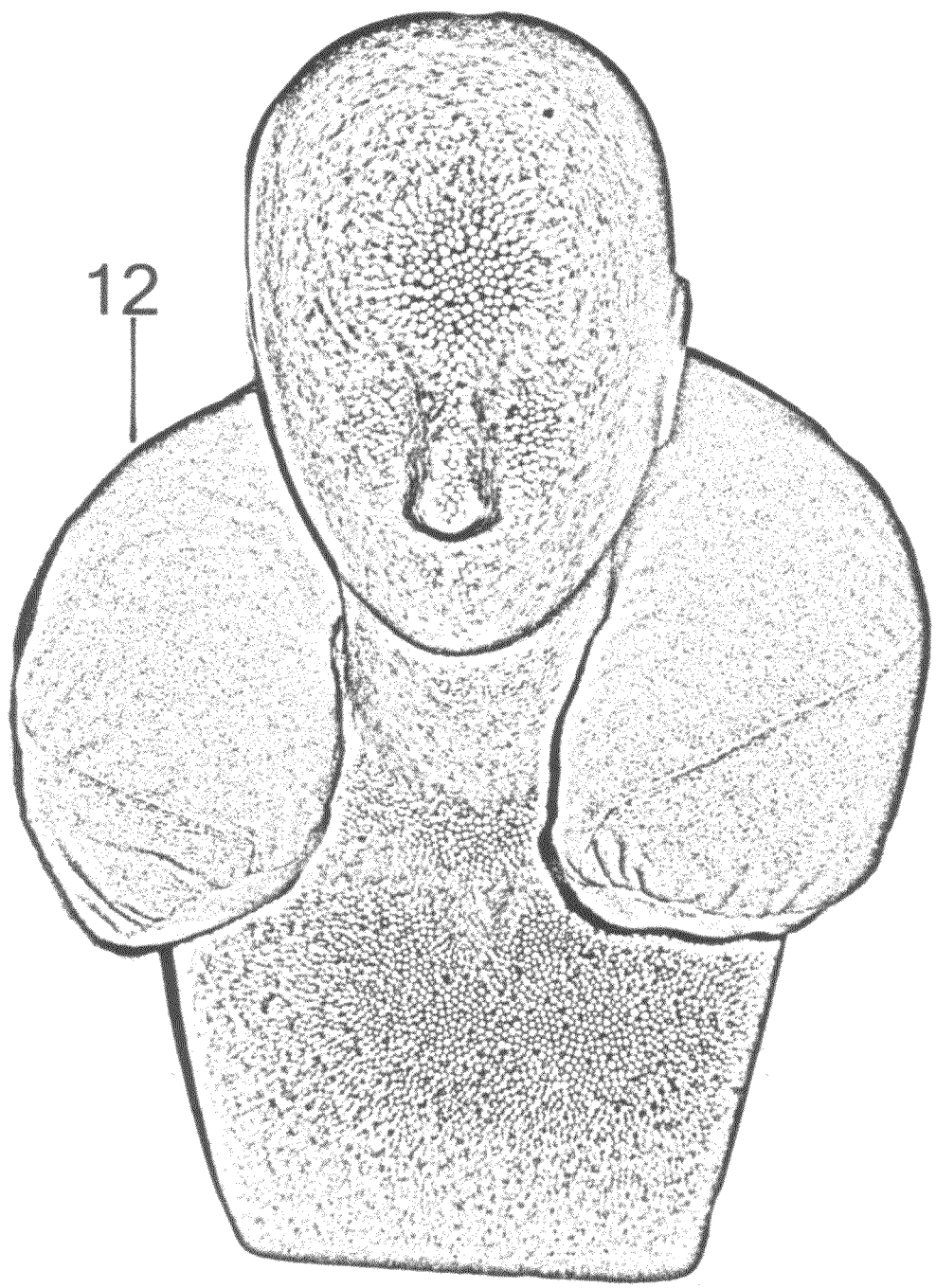
FIG. 10 illustrates ¾ back view of bone and strap system.

FIG. 10 illustrates ¾ back view of bone and strap system. Full listing of items is adjustable seat clips (1), adjustable seat straps (2), detachable clips (3), supportive seat brace (4), neck bone support (5), supportive arm strap (6), support belt (7), arm bone (8), upper back bone support (9), pillow (10), shoulder support padding (11), and pillow cover (12).

Figure 11:
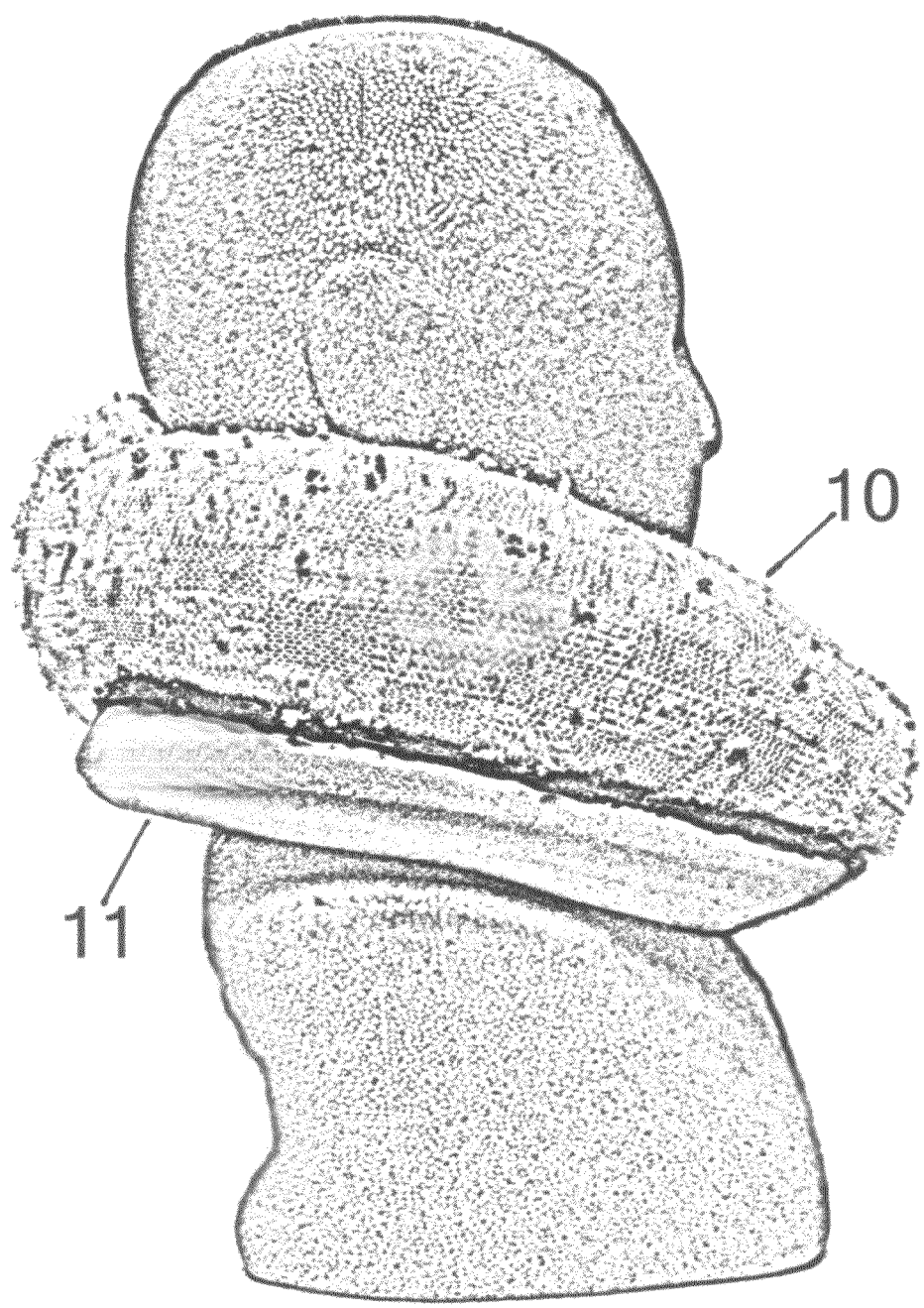
FIG. 11 shows side view of pillow, shoulder part, indicating pillow without bone and without cover (10), and shoulder support padding (11).

FIG. 11 shows side view of pillow, shoulder part, indicating pillow without bone and without cover (10), shoulder support padding (11).

Figure 12:
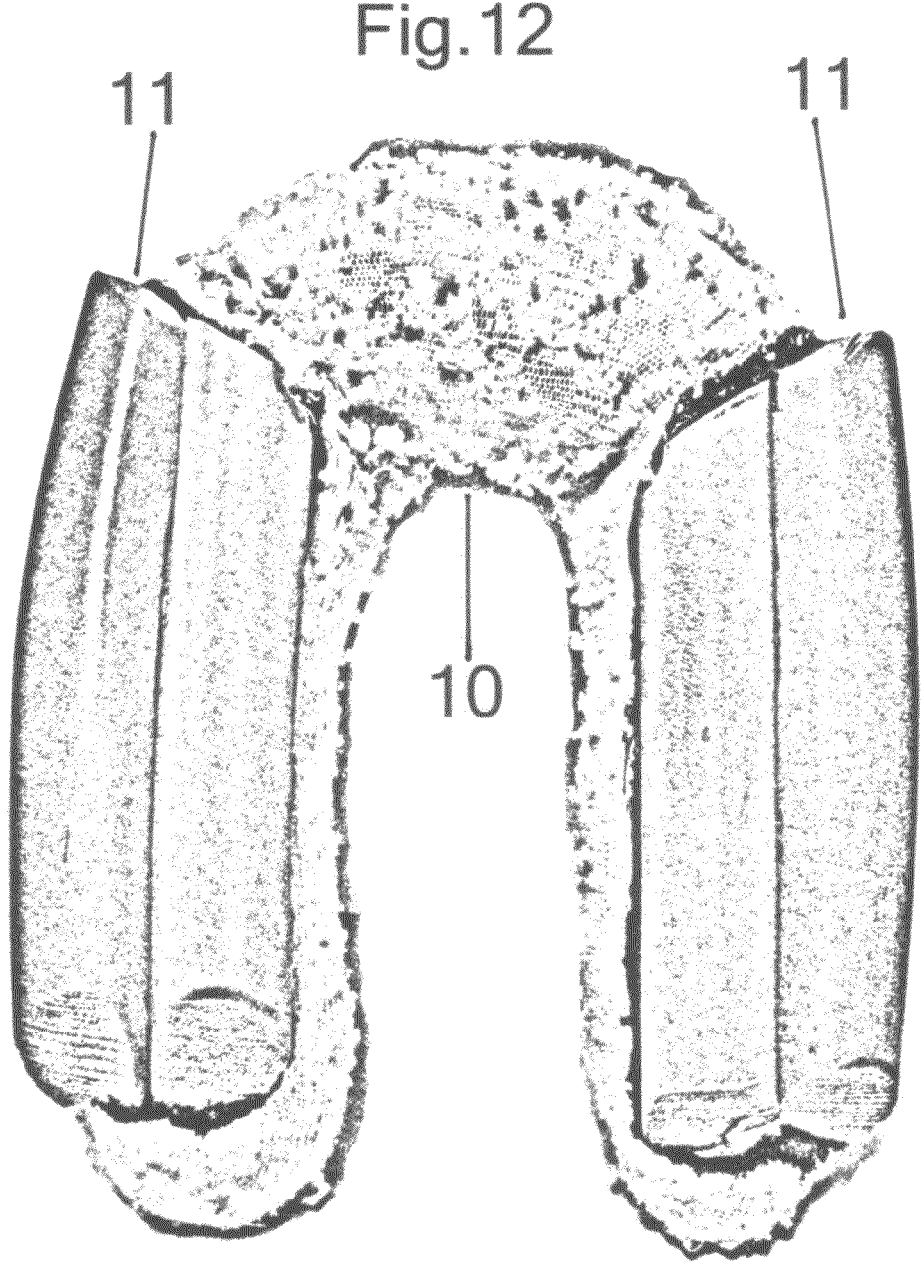
FIG. 12 shows a bottom pillow view.

FIG. 12 shows a bottom pillow view, indicating pillow without bone and cover (10), and shoulder support padding (11).

Figure 13:
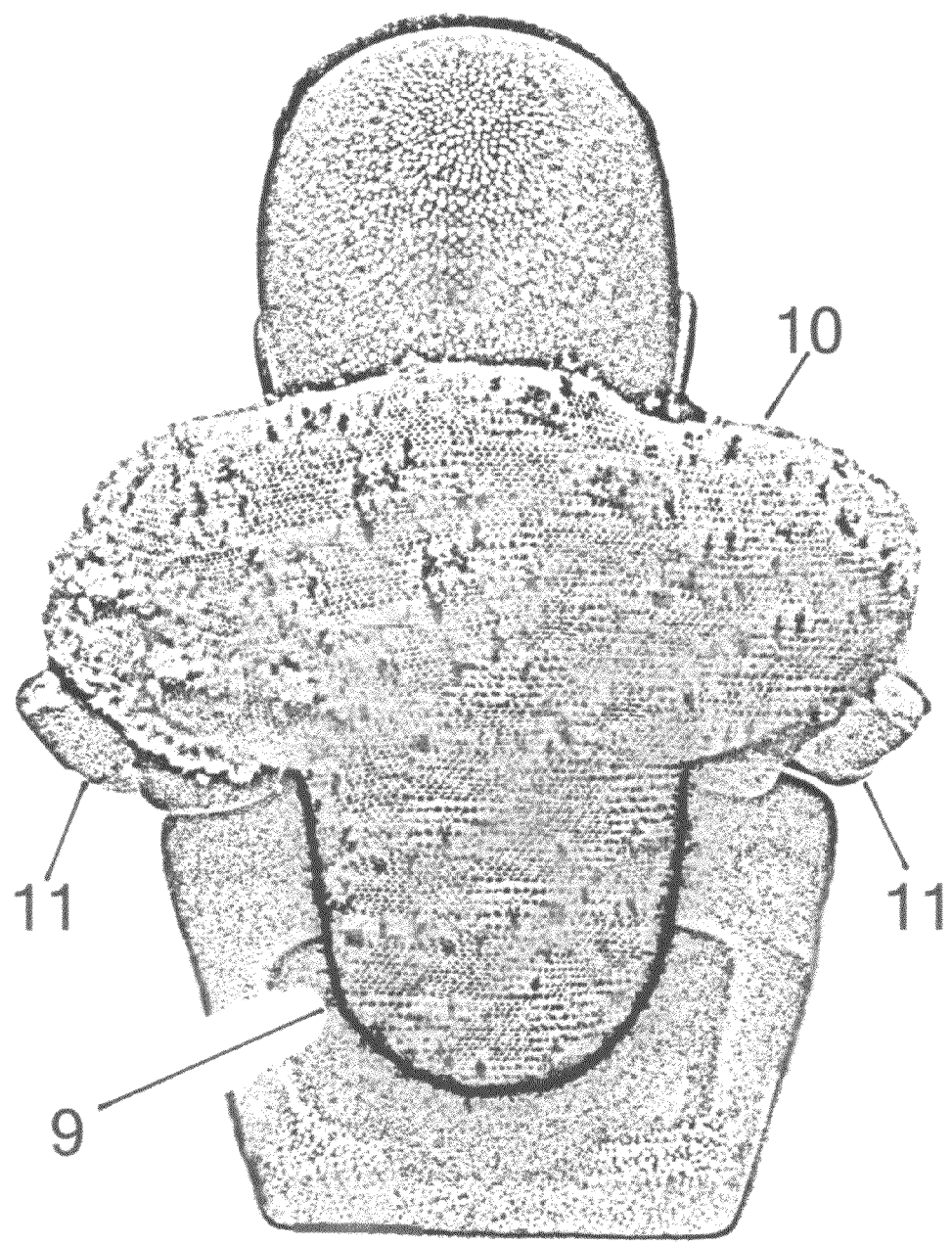
FIG. 13 shows a back view of pillow (without cover, and straps).

FIG. 13 illustrates a back view of pillow (without cover, and straps), indicating pillow (10), shoulder padding (11), upper back bone support inside pillow (9).

FIG. 14 illustrates a complete pillow and straps (back view without cover); indicating adjustable seat clips (1), adjustable seat straps (2), pillow (10), shoulder support padding (11), and upper back bone support in pillow (9).

Then, the parts indicated in the attached figures are explained in detail as below.

Adjustable Seat Clips (1):

The adjustable seat clips (1) are made of strong durable hard plastic. The clips are made of two pieces. One is the back clips which sets on the back of the seat is enclosed in a strap which is connected to the adjustable seat straps (2). Another is the front part of the clips which sets on the front part of the seat, and continues as supportive seat brace (4). The front clips slides into the back clips which makes it adjustable on the seat. The head weight on the pillow; because it is connected to the adjustable seat straps (2), will cause the back seat clips to come forward, and make the clips secure on the seat.

Adjustable Seat Straps (2):

The adjustable seat straps (2) are made of strong durable material. They are connected to the seat clips (1). They are made to be adjustable for any length, or height of the person using the pillow.

Detachable Clips (3):

The detachable clips (3) are made of a strong durable hard plastic. It is used to make Sleepy Heads Neck Pillow detachable from the adjustable clip/strap system.

Supportive Seat Brace (4):

The supportive seat brace (4) is made of strong durable hard plastic; it gives extra support on the front of the seat and keeps the clips closed by the weight of the head on the pillow.

Neck Bone Support (5):

The Neck Bone Support (5) is made of a strong durable hard plastic which the whole bone structure that consists of the three parts; (5), (8) and (9) which may be adjustable, is made of. It is the neck support of the bone structure of the pillow. It conforms, fits the shape of the neck which gives high support, and comfort to the neck of the pillow. The bone of the pillow is one piece that consists of three parts; part (5), part (8) and part (9).

Supportive Arm Strap (6):

The supportive arm strap (6) is made of strong durable material, which is the same material as all of the straps on the pillow. It wraps around each side of the arm bone (8), so that it gives extra support and balance keeping the pillow in a horizontal position. The supportive arm strap (6) is connected to the support belt (7).

Support Belt (7):

The Support Belt (7) is made of a strong durable material, which is the same material as all of the straps in the pillow. It is securely fixed through a hole in the back bone structure. The support belt (7) is connected to the supportive arm strap (6) which continues up to the detachable clips (3).

Arm Bone (8):

The arm bone (8) is part of the bone structure that is extended over the shoulder from the neck bone support (5). It is an arm shape structure which gives support to the head when the head is resting on the side.

Upper Back Bone Support (9):

The upper back bone support (9), a part of the bone structure support that is extended down the upper back; gives extra support to the neck, and upper back. All of the three parts of the born structure which may be adjustable (5), (8) and (9) combined together create a perfect balance, comfort to give the head, neck, and shoulders support with great stability on the pillow. The full bone structure support will be fully incased inside the pillow.

Pillow (10):

The pillow (10) is made up of form fitting foam pieces. The Pillow is firm, but because of the form fitting foam pieces it also conforms to the shape of neck, and face line. It is very comfortable all around the pillow. The user of the sleepy head and neck pillow won't be able to feel the hardness of the bone structure that is inside of the pillow.

Shoulder Support Padding (11):

The shoulder support padding (11) is made of a firm form fitting foam material which will be placed under the pillow on both shoulders. This support will give extra comfort and stability on the shoulders.

Pillow Cover (12)

The pillow cover (12) is made of very soft and comfortable material that will fit the pillow perfectly. The pillow cover is removable, and washable.

Until now, no one has invented a head and neck pillow, which is out on the market today, like the present invention.

The sleepy head and neck pillow of the present invention has three different uses. Sleep while sitting up during transportation (airplane, train, bus, car, etc.). It gives support to people who have neck injuries, during transportation (airplane, train, bus, car, etc.). While not using the clip/strap system, it can be used as a comfortable resting pillow.

The sleepy head and neck pillow of the invention will be useful to insurance companies because it will provide their customers with extra safety which will reduce the risk of neck injuries, therefore saving money for the insurance companies, and their customers. Whiplash victims can also use the sleepy head and neck pillow of the invention to ease their pain because it will give their neck support and comfort. Airline companies can also build sleepy head and neck pillow of the invention into the airplane seats so that the passengers will be able to sleep sitting up during flight with great comfort. The airline companies can also rent sleepy head and neck pillow of the invention on their flights for their passengers.

The sleepy head and neck pillow of the invention may be made in four different sizes. X-Small (infant), Small (Child), Medium (Adult), and Large (Adult). The pillow structure and shape may be exactly the same, only the size may be different.

| Full Listings of Items | |
| --- | --- |
| 1. | Adjustable Seat Clips |
| 2. | Adjustable Seat Straps |
| 3. | Detachable Clips |
| 4. | Supportive Seat Brace |
| 5. | Neck Bone Support |
| 6. | Supportive Arm Strap |
| 7. | Support Belt |
| 8. | Arm Bone |
| 9. | Upper Back Bone Support |
| 10. | Pillow |
| 11. | Shoulder Support Padding |
| 12. | Pillow Cover |

The invention claimed is:

1. A sleepy heads neck pillow for use in supporting the neck, head and upper back of a user, comprising a pillow with a substantially rigid bone structure support inside the pillow and a clip/strap system that is fixed to the bone structure, wherein the bone structure support is fully incased in the pillow, and the bone structure support comprises three parts; a neck bone support having a top edge, a bottom edge, a left edge and a right edge, wherein the neck bone support is configured to conform to and support the back of the neck of the user, a pair of arm bone supports respectively extending from the left and right edges of the neck bone support wherein a length of each arm bone support is substantially greater than a width of each arm bone support so that the arm bone supports are configured to extend forwardly of the shoulders of the user to support the user's head when the head is resting to the side, and an upper back bone support that is extended down at an angle from the bottom edge of the neck bone support so that the upper back bone support is configured to give extra support to the neck and upper back of the user, and the bone structure support is made of one piece.

2. The sleepy heads neck pillow according to claim 1, wherein said clip/strap system comprises a supportive adjustable strap which is connected to the clip, said adjustable strap being fixed to said bone structure.

3. A pillow for use in supporting the neck, head and upper back of a wearer configured to be positioned on the shoulders of a wearer and support the neck of the wearer, comprising:
a substantially rigid bone structure support fully incased inside said pillow, said bone structure support comprising a neck bone support having a top edge, a bottom edge, a left edge and a right edge, wherein the neck bone support is configured to conform to and support the neck of the wearer, a pair of spaced arm bones extending respectively from the left and right edges of said neck bone support wherein a length of each arm bone is substantially greater than a width of each arm bone so that the arm bones are configured to extend forwardly of the shoulders of the wearer to support the head of the wearer when the head is resting to the side, and an upper back bone support extending down at an angle from the bottom edge of said neck bone support and down the upper back so that the upper back bone support is configured to give extra support to the neck and the upper back of the wearer, and the bone structure support is made of one piece.

4. The pillow of claim 3, further comprising a strap system fixed to said bone structure support, said strap system comprising a clip.

5. The pillow of claim 3, wherein said neck bone support is C-shaped.

6. The pillow of claim 3, further comprising shoulder support padding on said pillow configured to contact the wearer's shoulders.

7. The pillow of claim 3, further comprising a pillow cover covering said pillow.

* * * * *